United States Patent [19]
Hemmings et al.

[11] Patent Number: 6,054,285
[45] Date of Patent: Apr. 25, 2000

[54] SCREENING METHOD

[75] Inventors: Brian Arthur Hemmings, Bettingen; Matthias Frech, Basel, both of Switzerland

[73] Assignee: Novartis AG, Basel, Switzerland

[21] Appl. No.: 09/091,058

[22] PCT Filed: Nov. 5, 1996

[86] PCT No.: PCT/EP96/04814

§ 371 Date: Jun. 10, 1998

§ 102(e) Date: Jun. 10, 1998

[87] PCT Pub. No.: WO97/22717

PCT Pub. Date: Jun. 26, 1997

[30] Foreign Application Priority Data

Dec. 15, 1995 [GB] United Kingdom .................. 9525703

[51] Int. Cl.[7] .............................. C12N 9/12; C12Q 1/48
[52] U.S. Cl. .................... 435/15; 435/194; 435/320.1; 435/252.3; 436/86
[58] Field of Search ................. 435/194, 320.1, 435/252.3, 15; 436/86

[56] References Cited

U.S. PATENT DOCUMENTS

| | | | |
|---|---|---|---|
| 5,266,565 | 11/1993 | Lacoste et al. | 514/114 |
| 5,278,154 | 1/1994 | Lacoste et al. | 514/114 |
| 5,385,915 | 1/1995 | Buxbaum et al. | 514/313 |
| 5,422,125 | 6/1995 | Skyler et al. | 424/646 |

FOREIGN PATENT DOCUMENTS

| | | |
|---|---|---|
| 0 245 979 | 11/1987 | European Pat. Off. . |
| 0 264 278 | 4/1988 | European Pat. Off. . |
| 0 521 787 | 1/1993 | European Pat. Off. . |
| 0 551 200 | 7/1993 | European Pat. Off. . |
| WO 91/19008 | 12/1991 | WIPO . |
| WO 92/09891 | 6/1992 | WIPO . |
| WO 95/13820 | 5/1995 | WIPO . |
| WO 97/18303 | 5/1997 | WIPO . |
| WO 97/22716 | 6/1997 | WIPO . |

OTHER PUBLICATIONS

Boudewijn Burgering et al., Laboratory for Physiological Chemistry, Nature—vol. 376, pp. 599–603.
Kohn et al., The EMBO Journal, vol. 14, No. 17, pp. 4288–4295, 1995.
Jenö et al., Proc. Natl. Acad. Sci. USA, vol. 85, pp. 406–410, Jan. 1988.
Chambers et al., Molecular Pharmacology, vol. 41, No. 6, pp. 1008–1015, 1992.
Persaud et al., Biochem J., vol. 319, pp. 119–124, (1996).
Carey et al., Diabetes, vol. 44, 1995, pp. 682–688, Jun. 1995.
Andjelkovic et al., Proc. Natl. Acad. Sci. USA, vol. 93, pp. 5699–5704, Jun. 1996.
Derwent Abstract 91–019158/03, JP 02292217, Aug. 5, 1989.
Jones et al., Cell Regulation, vol. 2, pp. 1001–1009, Dec. 1991.
Tyers et al., Nature vol. 333, pp. 470–473, Jun. 1988.
Cross et al., Nature, vol. 378, vol. 21/28, pp. 785–789 (1995).
Franke et al., Cell, vol. 81, pp. 727–736 (1995).

*Primary Examiner*—Rebecca E. Prouty
*Assistant Examiner*—M. Monshipouri
*Attorney, Agent, or Firm*—Gregory D. Ferraro

[57] ABSTRACT

The invention concerns a method for screening a compound which is a candidate modulator of signal response comprising the steps of; (a) incubating the compound with the PH domain of a signaling molecule which is capable of fluorescing; (b) determining the phospholipid-induced modulation in florescence of the PH domain, an alteration of the florescence in the presence of the compound being indicative of a functional interaction between the compound and the PH domain.

7 Claims, No Drawings

SCREENING METHOD

This is a 371 of PCT/EP96/04814, filed Nov. 5, 1996.

The present invention concerns a method for screening for compounds which are potential modulators of signalling pathways involving the serine/threonine kinase RAC and to the use of the pleckstrin homology domain of RAC-PK in such a method.

The RAC subfamily of serine/threonine protein kinases [Jones, et al. (1991) *Proc. Nati. Acad. Sci. U. S. A.* 88, 4171–4175; Jones, et al. (1991) *Cell Reg.* 2, 1001–1009], which are closely related to the cAMP-dependant protein kinase (PKA) and $Ca^{2+}$/phospholipid dependant protein kinase (PKC) families in their kinase domain, contain an amino-terminal pleckstrin homology (PH) domain [Haslam, et al (1993) *Nature* 363, 309–310]. The human RAC-PKα isoform is the protooncogenic form of v-akt, which encodes a complete RAC-PK with the addition of a truncated gag sequence at the amino-terminus providing a myristylation sequence.

The PH domain was originally identified as an internal repeat, present at the amino and carboxy-termini of pleckstrin, a 47 kDa protein which is the major PKC substrate in activated platelets [Tyers, et al. (1988) *Nature* 333, 470–4731]. The superfamily of PH domain containing molecules consists of over 60 members, including serine/threonine protein kinases (RAC-PK, Nrk, βARK, PKCμ), tyrosine protein kinases (Btk, Tec, Itk), GTPase regulators (ras-GAP, ras-GRF, Vav, SOS, BCR), all known mammalian phospholipase Cs, cytoskeletal proteins (β-spectrin, AFAP-110, syntrophin), "adapter" proteins (GRB-7, 3BP2) and kinase substrates (pleckstrin, IRS-1).

While the PH domain structure has been solved for β-spectrin, dynamin and pleckstrins amino-terminal domain, its precise function remains unclear. The presence of PH domains in many signalling and cytoskeletal proteins implicates it in mediating protein-protein interactions. Indeed, the PH domain of the β-adrenergic receptor kinase (βARK) appears partly responsible for its binding to the βγ-subunits of the heterotrimeric G-proteins associated with the β-adrenergic receptor, while the PH domain of the Bruton's tyrosine kinase (Btk) appears to mediate an interaction with PKC. Several PH domains have been shown to be able to bind phosphatidyl-inositol-(4,5)-bisphosphate in vitro, although weakly. We have now shown that the PH domain of RAC-PK binds phospholipid with high affinity, which suggests that RAC-PK my be membrane-bound in vivo via the PH domain. Moreover, binding of phospholipid to the RAC-PK PH domain quenches the intrinsic Trp fluorescence thereof.

SUMMARY OF THE INVENTION

According to a first aspect of the invention, therefore, we provide a method for screening a compound which is a candidate modulator of signal response comprising the steps of:

(a) incubating the compound with the PH domain of a signalling molecule which is capable of fluorescing;

(b) determining the phospholipid-induced modulation in the fluorescence of the PH domain, an alteration of the fluorescence in the presence of the compound being indicative of a functional interaction between the compound and the PH domain.

DETAILED DESCRIPTION OF THE INVENTION

The observed high affinity binding of phospholipid to the N-terminus of the PH domain of signalling molecules suggests that the PH domain functions as a membrane anchor for the molecules. Interaction of molecules with the cell membrane is believed to be important for the stable interaction thereof with membrane bound partners in signalling pathways, such that disruption of this interaction will lead to modulation of the signalling effect through the dissociation of the signalling molecule from the cell membrane. The modulation could be either down-regulating, for example if the otherwise stable interaction of the molecule with membrane-bound partners is a stimulatory interaction, or up-regulating, in the event that the interaction is an inhibitory interaction.

Accordingly, compounds which affect the binding of the PH domain to phospholipids present in the cell membrane are potential modulators of signal response.

Such compounds could be agents which cause a conformational change in the PH domain, either increasing or decreasing its affinity for phospholipid, or compounds which compete directly for binding of the PH domain to the cell membrane, for example phospholipid molecules or inositol phosphates.

The effect on the PH domain of the molecule may be direct or indirect. In other words, the compound may interact directly with the PH domain to alter its affinity for membrane phospholipid, or it may exert its effect without direct interaction with the PH domain, for example by interacting with another domain of the molecule and thereby influencing the PH domain, for example causing a conformational change. Compounds which have a direct effect on the PH domain may be screened using isolated PH domain, whereas compounds having an indirect effect thereon should be screened using intact the signalling molecule.

Signalling molecules according to the invention comprise all molecules involved in signalling pathways which possess a PH domain, although the method is clearly only practicable with those PH domains having a fluorescent group in the phospholipid binding amino terminus. Such molecules are characterised by a trp residue, homologous to $Trp^{22}$ in RAC-PK.

Preferably, the method of the invention is applied to protein kinases and their substrates, which are implicated in intracellular signalling and growth control. Advantageously, the method is applicable to RAC kinase and its PH domain, which shows a high affinity for phospholipid and fluoresces via $Trp^{22}$ in a phospholipid-binding dependent manner.

Isolated PH domain for use in the present invention may be prepared as set forth in by recombinant expression employing an extension of at least three hydrophilic amino acids on the C-terminus of the domain. It is found that the yield and solubility of the domain in bacterial cell culture is thereby increased.

Preferably, between three and ten additional amino acid residues are present at the C-terminal end of the domain. Advantageously, three to six residues are added. In general, the greater the number of residues present, the greater the increase in hydrophilicity conferred thereby. However, this must be balanced by the clearly advantageous avoidance of an excessively long addition to the gene product.

Any hydrophilic amino acid is suitable for use in the present invention. In general, hydrophilic amino acids possess polar R-groups which improve the solubility thereof in water. Such amino acids may possess uncharged R-groups, such as glycine, serine or threonine, or charged R-groups, such as aspartic acid or glutamic acid, which are negatively charged (acidic) and lysine or arginine, which are positively charged (basic). Preferred, however, are basic amino acids such as lysine, arginine and histidine. Most preferred is lysine.

Where more than one additional amino acid is used, the additional amino acids may be the same or different. For example, it is possible to use three lysines. Alternatively, two lysines and an arginine residue may be combined.

The expression system for use in the present invention is in essence a conventional expression system which is modified by standard methodology to conform to the requirements set forth herein. In practice, the invention may be effected starting with any expression system known in the art which entail the intracellular production of a heterologous polypeptide in a bacterial host cell. The bacterial host cell may be any bacterial cell known for use in the production of heterologous polypeptides, but E.coli and B. subtilis cells are preferred. E. coli is especially preferred.

Typically, the bacterial host cell is transformed with an expression vector comprising a coding sequence encoding the heterologous polypeptide, to which the requisite number of nucleotides encoding the hydrophilic amino acids to be added to the C-terminus have been appended. Addition of nucleotides to the coding sequence may be carried out by conventional means, such as insertion of oligonucleotide linkers or site-directed mutagenesis. In an alternative embodiment, however, an expression vector may be constructed in which the required nucleotides encoding a C-terminal hydrophilic extension are already in place, upstream of a suitable stop codon, so that a sequence encoding the heterologous polypeptide may be inserted directly upstream thereof by conventional cutting and pasting with restriction enzymes.

The recovery of soluble PH domain may be further enhanced by expression thereof in the form of a fusion protein. This technique involves the expression of the domain as a fusion with a further polypeptide. Usually, only the first few amino acids of the further polypeptide are present, fused to the N-terminus of the heterologous polypeptide. The fusion is made at the DNA level taking care to preserve the correct reading frame in the domain, such that the composite gene is expressed to produce the fusion protein.

Fusions may be made with a suitable gene, which may be of natural, such as bacterial, or artificial origin. Thus, for example, a fusion may be made with a β-galactosidase or a glutathione-S-transferase (GST) gene. Preferably, however, an artificial fusion is created using an artificial gene. Advantageously, the composition of the further polypeptide encoded by the artificial gene is selected to further improve the solubility of the fusion protein expression product. Advantageously, therefore, the further polypeptide comprises hydrophilic amino acids as defined hereinbefore. The further polypeptide may comprise any reasonable number of such amino acids, but a range of three to ten is preferred, with five to ten being more preferred. Advantageously, the further polypeptide comprises about six amino acids.

Preferably, the amino acids which comprise the further polypeptide are basic amino acids. Histidine is advantageously used.

Advantageously, therefore, the expression vector is adapted to express heterologous polypeptides as fusion proteins. A number of such vectors are available commercially. Particularly useful in the context of the present invention are vectors expressing fusions with further polypeptide of a hydrophilic nature, such as the pRSET vector from Invitrogen.

An advantage of using a further polypeptide which is comprised of hydrophilic amino acids is that both ends of the fusion protein are hydrophilic in character, thus further enhancing the increased solubility of the heterologous polypeptide.

Terminally added amino acids according to the invention, including the further polypeptides added as part of fusion proteins, may be removed during or after purification of the heterologous polypeptide from the cell culture by terminal digestion, enzymatic cleavage as normally carried out with fusion proteins or by other means. In the case of enzymatic cleavage, the terminal additions will advantageously comprise cleavage sites for restriction enzymes or chemical modifying agents to permit removal of the added amino acids.

The expression vector used in the invention comprises the regulatory sequences required to achieve expression in the intended host cell. In addition, it may contain the necessary sequences required for plasmid replication in order to exist in an episomal state, or it may be designed for chromosomal integration.

Regulatory sequences will include a promoter capable of driving the sequence encoding the heterologous polypeptide. For example, strong viral promoters such as the SV40, adenovirus or hCMV promoters may be used. However, expression of soluble heterologous polypeptide may be further enhanced through the use of an inducible promoter. Inducible promoters are promoters which are inactive or only active at low levels until induced by the administration of a particular stimulus to the host cell. The main advantage thereof is that they permit culturing of the cell to the required cell density before induction of heterologous polypeptide expression, thereby avoiding placing excessive metabolic load on the cell until cell growth is complete. Numerous inducible promoters are available in the art, and in general bacterial promoters which control expression of the synthesis of non-essential nutrients are inducible. The trp promoter of E. coli, for example, is induced at low concentrations of Trp in the growth medium. The β-galactosidase (lacZ) promoter of E. coli, on the other hand, is inducible by the administration of IPTG. Where a viral promoter is used, inducibility may be achieved by means of regulation of the supply of transactivators required by certain viral promoters. The adenovirus immediate-early promoter, for example, is transactivated by the E1 A gene product.

Bacterial culture is normally carried out at 37° C., and induction of an inducible promoter such as the IacZ promoter may be carried out at the normal culturing temperature. However, we have found that by inducing expression at a reduced temperature both yield and solubility of the product may be increased. Preferably, therefore, induction is carried out at below 37° C. The preferred range is 20 to 33° C., with 24° C. being the most preferred temperature. Preferably, the induction temperature is maintained over the period during which the heterologous polypeptide is expressed.

Since the heterologous polypeptide produced according to the invention is soluble but located intracellularly, recovery thereof requires lysis of the bacterial cell wall and recovery of the heterologous polypeptide from the cell lysate. Conventional recovery procedures may be used, typically involving removal of particulate cell residue by centrifugation and subsequent purification of the protein by chromatographic procedures. The inclusion of terminal hydrophilic amino acids may significantly alter the isoelectric point of the polypeptide, allowing enhanced affinity purification on a cation exchange column at neutral pH. Moreover, inclusion of histidine as a hydrophilic amino acid means that purification may be easily achieved on a Ni(II) affinity column by virtue of the His tag on the heterologous polypeptide. Further conventional purification techniques may be practised, such as size exclusion chromatography or affinity chromatography, in order to prepare pure heterologous polypeptide.

Where a small quantity of PH domain suffices, however, PH domain may be obtained by expressing a nucleic acid sequence encoding it in bacterial cell culture in the form of a simple fusion protein which is subsequently cleaved according to techniques known in the art. For example, amino acids 1–131 of RAC-PK, which encode the PH domain, may be expressed as a fusion with glutathione-S-transferase, subsequently cleaving the fusion protein with thrombin and isolating the domain by protein purification techniques such as FPLC. This method gives a relatively small yield of pure soluble PH domain.

RAC-PK for use in the present invention may be prepared as set forth in UK patent application 9525702.8 (Ciba-Geigy AG), filed on Dec. 15th 1995. Alternatively, RAC-PK may be expressed in recombinant cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) *PNAS (USA)* 89, 2679–2683). The baculovirus vector of choice (reviewed by Miller (1988) *Ann. Rev. Microbiol.* 42,177–199) is *Autographa californica* multiple nuclear polyhedrosis virus, AcMNPV.

Typically, the heterologous gene replaces at least in part the polyhedrin gene of AcMNPV, since polyhedrin is not required for virus production. In order to insert the heterologous gene, a transfer vector is advantageously used. Transfer vectors are prepared in *E. coli* hosts and the DNA insert is then transferred to AcMNPV by a process of homologous recombination. Baculovirus techniques useful in the present invention are standard and well known in the art, and are reviewed in O'Reilly et a., (1994) Baculovirus expression vectors; A laboratory manual, Oxford University Press Inc., NY, USA, as well as in literature published by suppliers of commercial baculovirus kits (e.g. Pharmingen).

Fluorescence of Trp residues in a PH domain may be detected by exciting the molecule to fluoresce at the appropriate frequency and monitoring the emission. RAC-PK, for example, fluoresces at 345 nm when excited at 290 nm. Techniques for monitoring protein fluorescence are widely known in the art.

The invention is further described, for the purposes of illustration only, in the following examples.

COMPARATIVE EXAMPLE 1

Expression of PH Domain

The PH domain of RAC-PK is expressed in bacterial cell culture as a non-fusion protein as follows: bacteria (XL1 blue; Stratagene) are transformed with the constructs pRK-PH 110 or pRK-PH131. pRK-PH110 and pRK-PH131 contain amino acids 1–110 and 1–131 of human RAC-PKα respectively. They are constructed by isolating the NdeI-PflMI and NdeI-AlwNI fragments from pRK-hRAC-PKα [Jones, et al., (1991) *Proc. Natl. Acad. Sci. U.S.A* . 88, 4171–4175] and ligating them into the NdeI-EcoRl sites of pRK172 [McLeod et al, (1987) *EMBO J.* 6, 729–736] using a PflMI-EcoRI linker [5' oligo 5'-GTG GCT GAC GGC CTC TGA G-3' (SEQ ID No:7), 3' oligo 5'-AAT TCT CAG AGG CCG TCA GCC ACA GT-3' (SEQ ID No:8)] and an AlwNI-EcoRI linker [5' oligo 5'-CTT GAT GAG-3' (SEQ ID No:9), 3' oligo 5'-AAT TCT CAT CM GCC C-3' (SEQ ID No:10)]. General molecular biological techniques are performed as previously described [Sambrook, et al., (1989) *Molecular Coning: A Laboratory Manual*, 2nd Ed., Cold Spring Harbor Laboratory, Cold Spring Harbor, NY; Davis, et al., (1986) *Basic Methods in Molecular Biology*. Elsevier Science Publishing Co., New York, N.Y.].

Bacteria (JM 109) are grown in LB medium at 37° C. in an air-shaker with rotation at 150 rpm. Induction with 0.1 mM IPTG of strains carrying the plasmids listed above is commenced when the cultures reach an $O.D._{600\ nm}$ of 1.0, for 0–16 hr at 37° C. Aliquots of the cultures are harvested at various times points, washed with one volume of PBS and then stored at −80° C. before being analysed. Cell pellets are lysed in buffer (PBS, 1% Triton X-100, 1 mM benzamidine, 0.1 mM PMSF) using a French Press. The lysate is then centrifuged at 12000 X g to separate soluble and insoluble protein fractions. The insoluble pellet is resuspended in the above buffer. Protein in the soluble and insoluble fractions are analysed by coomassie stained SDS-PAGE gels and quantitated using the BIO-RAD protein quantification assay. Protein preparations are also subjected to Western blotting analysis [Harlow, E., and Lane, D. (1988) *Antibodies—A Laboratory Manual*, Cold Spring Harbor Laboratory, Cold Spring Harbor, N.Y.] using a polyclonal rabbit antiserum directed against bacterially expressed full-length human RAC-PKα raised by injecting rabbits subcutaneously with RACα protein and purified by precipitation using 50% $(NH_4)_2SO_4$ followed by affinity chromatography on Protein-A Sepharose (Pharmacia). The secondary antibody is a horse radish peroxidase coupled anti-rabbit antibody (Amersham) which is detected using the ECL method (Amersham) by autoradiography.

This method produced significant amounts of protein (~20 mg/l) but in a totally insoluble form.

Example 2

The PH domain of RAC-PK is expressed as a fusion polypeptide with a $(His)_6$ tag.

pRSET-PH110 and pRSET-PH131 contains in-frame fusions of amino acids 1–110 and 1–131 of human RAC-PKa, respectively, with an amino-terminal $(HIS)_6$-tag. They are constructed by inserting the NdeI-EcoRI fragment of pRK-PH110 or pRK-PH131, respectively, into the BamHI-EcoRI sites of pRSET-A using a BamHI-NdeI linker [5' oligo 5'-GAT CCG CTG GAG C-3' (SEQ ID No:13); 3' oligo 5'-TAG CTC CAG CG-3' (SEQ ID No: 14)].

pRSET-PH112 contains an in-frame fusion of amino acids 1–112 of human RAC-Pkα with an amino-terminal $(HIS)_6$-tag. It is constructed by subcloning a NdeI-PflmI fragment of pRK-hRAC-Pkα into the BamHI-EcoRI sites of pRSET-A using a BamHI-NdeI linker (see above) and a PflMI-EcoRI linker [5' oligo 5'-GTG GCT GAC GGC CTC MG MG TGA G3' (SEQ No:18); 3' oligo 5'-AAT TCT CAC TTC TTG AGG CCG TCA GCC ACA GT-3' (SEQ ID No:15)].

Expression conditions were as for comparative Example 1, except that bacterial strains JM109(DE3), BL21 (DE3) pLysS and BL21 (DE3)pLysE (Invitrogen) are used for the production of $(HIS)_6$-tagged proteins.

The pRSET constructs (pSRET-PH110, pRSET-PH112 and pRSET-PH131) produce significant amounts of protein (~2 mg/l) that is partially (~20%) soluble. The strain BL21 (DE3)pLysE produces result indistinguishable from that of BL21 (DE3)pLysS. However, the strain JM109(DE3) produced less protein that is also less soluble and not inducible to the same extent as the BL21 strains.

Example 3 pRSET-PHQ116KKK contains an in-frame fusion of amino acids 1–116 of human RAC-Pkα with an amino-terminal $(HIS)_6$-tag, the addition of three lysines at the carboxyl-terminus, and the internal methionine, amino acid number 63, is mutated to a glutamine. It is constructed by inserting a PvuII-BbsI linker [5' oligo 5'-CTG CM MG ACG G-3' (SEQ ID No:16); 3' oligo 5'-CGC TCC GTC TTT TGC AG-3' (SEQ ID No:17)] into pRSET-PH131 digested with PvuII-BbsI. A PflMI-EcoRI linker [5' oligo 5'-GTG GCT GAC GGC CTC AAG AAG CAG AAG AAG AAG TGA G-3' (SEQ ID No:18); 3' oligo 5'-MT TCT CAC TTC TTC TTC TGC TTC TTG AGG CCG TCA GCC ACA GT-3' (SEQ ID No:19)] is then inserted into the resultant plasmid at its PflMI-EcoRI sites. The C-terminal differences between the pRSET vectors employed are represented in Table 1.

TABLE 1

| | | |
|---|---|---|
| PH110 | ... WTTAIQTVADGL | (SEQ ID No:20) |
| PH112 | ... WTTAIQTVADGLKK | (SEQ ID No:21) |
| PH131 | ... WTTAIQTVADGLKKQEEEEMDFRSGSPSDNSGA | (SEQ ID No:22) |
| PHQ116KKK | ... WTTAIQTVADGLKKQKKK | (SEQ ID No:23) |

Summary of differences between pRSET expression constructs containing various carboxy-terminal elements.

Using expression conditions as for Example 3, the production from pRSET-PHQ116KKK is significant (~5 mg/l) and almost all is soluble. Induction at 24° C. as compared to 37° C. also increases production and solubility. Production reaches at peak around two hours after induction at 24° C.

A large scale production (20 L) of BL21 (DE3)pLysS transformed with pRSET-PH116KKK by two hours induction at 24° C. is used to purify ~100 mg of the protein. The presence of the $(HIS)_6$ tag allows purification on the Ni(II) affinity column as follows: the soluble fraction of protein from BL21 (DE3)pLysS cells carrying the plasmid pRSET-PHQ116KKK harvested after 2 hours of induction with 0.1 mM IPTG at 24° C. and lysed in 20 mM phosphate buffer pH 7.2, 1.0 M NaCl, 1 mM benzamidine, 0.1 mM PMSF is loaded onto the column. The column, a 5 ml High-Trap metal cheating column (Pharmacia) is prepared as described by the manufacturer to contain Ni(II) ions. After loading the column with the sample it is washed sequentially with 5 bed volumes each of equilibration buffer (20 mM phosphate buffer pH 7.2, 1.0 M NaCl), ammonia buffer (20 mM phosphate buffer pH 7.2, 1.0 M $NH_4Cl$), low pH buffer (20 mM phosphate buffer pH 3.5, 0.5 M NaCl) and finally stripping buffer (20 mM phosphate buffer pH 7.2, 1.0 M NaCl, 50 mM EDTA). The eluted fractions are then analysed by SDS-PAGE.

This produces an approximately 50 fold purification. The high isoelectric point of the fusion protein (pI 9.6) allows the use of a cation exchange column to greatly enrich the protein a further 50 fold, as follows: the sample is equilibrated in buffer (50 mM Tris-HCI pH 7.0, 0.1 M NaCl, 2 mM EDTA, 1 mM DTT) by dialysis and loaded onto a 50 ml High-load-S cation exchange column (Pharmacia) which is equilibrated in the same buffer. Proteins are then eluted from the column with an ascending linear gradient of NaCl from 0.1 to 1.0 M in the above buffer. The column is connected to an FPLC system (Pharmacia). Collected fractions are then analysed by SDS-PAGE.

The third step is purification on a 1 l sephacryl S-300 HR gel-filtration column (Pharmacia). The sample is conceritrated to 5 ml (5 mg/ml) using an ultrafiltration unit (Pharmacia) and then applied to the column equilibrated in 20 mM Tris-HCl pH 7.0, 0.2 M NaCl, 2 mM EDTA, 1 mM DTT. Protein is eluted with the same buffer and fractions are analysed by SDS-PAGE.

This third purification step on the gel-filtration column produces an apparently homogeneous preparation. The purified protein is confirmed as the protein of interest by Western blot analysis using a human RAC-Pkα specific polyclonal antiserum. Amino terminal peptide sequencing of the purified protein shows identical to that of the predicted sequence.

Example 4
Preparation of RAC-PK PH Domain as a GST Fusion

General molecular biological techniques are performed as previously described [Maniatis, et al., (1982) *Molecular Coning: A Laboratory Manual*, Cold Spring Harbor Laboratory, Cold Spring Harbor, N.Y.; Sambrook et al., (1989) *Molecular Coning: A Laboratory Manual*, p.441, 2nd Ed., Cold Spring Harbor Laboratory, Cold Spring Harbor, N.Y.; Davis, et al., (1986) *Basic Methods in Molecular Biology*. Elsevier Science Publishing Co., New York, N.Y.].

The glutathione-Stransferase (GST) fusion vector pGEX-2T is obtained from Dr. P Matthias (FMI, Basel, Switzerland). pRKPH131 contains amino acids 1–131 of human RAC-Pkα (SEQ ID NOs. 1 and 2). It is constructed by isolating the NdeI-AlwNI fragment from pRK-hRAC-Pkα [Jones, et al., (1991) *Proc. Natl. Acad. Sci. U.S. A.* 88,4171–4175] and ligating it into the NdeI-EcoRI sites of pRK172 using an AlwNI-EcoRI linker [5' oligo 5'-CTT GAT GAG-3' (SEQ ID No:3), 3' oligo 5'-AAT TCT CAT CM GCC C-3' (SEQ ID No:4)].

pRSET-PH131 contains in-frame fusions of amino acids 1–131 of human RAC-Pkα with an amino-terminal $(HIS)_6$-tag. It is constructed by inserting the NdeI-EcoRI fragment of pRK-pRK-PH131, into the BamHI-EcoRI sites of pRSET-A (Invitrogen) using a BamHI-NdeI linker [5' oligo 5'-GAT CCG CTG GAG C-3' (SEQ ID No:5); 3' oligo 5'-TAG CTC CAG CG-3' (SEQ ID No:6)]. pGEX-PH131 contains an in-frame fusion of amino acids 1–131 of human RAC-Pkα with GST. It is constructed by subcloning a BamHI-EcoRI fragment from pRSET-PH131 into the BamHI-EcoRI sites of pGEX-2T.

The GST-RAC-PK fusion protein encoding expression vectors are expressed in *E. coli* cells follows: bacteria (JM109) are grown in LB medium at 37° C. in an air-shaker with rotation at 150 rpm. Induction with 0.1 mM IPTG of strains carrying the plasmids listed above is commenced when the cultures reach an $O.D._{600 nm}$ of 0.8, for 3hrs at 25° C. Cell pellets are lysed in buffer (PBS, 1% Triton X-100, 1 mM benzamidine, 0.1 mM PMSF) using a French Press. The lysate is then centrifuged at 12000×g, +5 min., 4° C., to separate soluble and insoluble protein fractions. The GST fusion protein is precipitated or bound to glutathione coupled to agarose, washed, eluted with glutathione, treated with thrombin to remove the GST fusion peptide and concentrated on Mono-Q by FPLC according to standard methodology.

The pGEX-PH131 construct in JM109 produces soluble protein that is easily purifiable but the yield is not very high (200 µg/l).

Example 5
Production of RAC Drotein Kinase

Full-length human RAC-PKα is expressed and purified from a baculovirus system. Briefly, a baculovirus is constructed by co-transfection of Sf9 cells with pVL1392-hRAC-Pkα and wild-type baculovirus AcMNPV DNA, purified by limiting dilution and detected by dot-blot hybridisation. The purified virus is used to produce human RAC-Pkα in Sf9 cells. The human RAC-Pkα is purified by sequential anion exchange, phospho-cellulose and gel filtration chromatography.

Example 6
Fluorescence of RAC-PK PH Domain

Purified PH domain obtained according to Example 1 is incubated at a concentration of 1.4 µM in 10 mM Hepes/NaOH, pH 7.0, 10 mM MgCl$_2$, at 25° C. When excited at 290 nm, using a slit width of 5.0 nm and an emission slit width of 6.5 nm, peak fluorescence of approximately 800 RU is observed at 345 nm.

Example 7
Phospholipids and Inositol Phosphates Reduce Fluorescence

Under the same conditions as Example 3, the RAC-PK PH domain is incubated in the presence of varying concentrations of phospholipids and inositol phosphates and fluorescence is measured. Peak fluorescence remains at 345 nm, but is reduced in according to the concentration of the lipid.

The maximal achievable quenching, in all cases, is 30%. In the case of Ptd-Ins (3,4,5) trisphosphate, quenching of 345 nm fluorescence of 100 nM RAC-PK PH domain incubated in Hepes/MgCl$_2$ as above ranges from nil at 0µM to virtually 100% of maximal at 6 µM. From the signal reduction, the dissociation constant for the lipids and inositol phosphates can be calculated and is set out in Table 1.

TABLE 1

| Compound | Dissociation Constant (µM) |
| --- | --- |
| Ptd-Ins (4,5) bisphosphate | 0.40 |
| Ptd-Ins (3,4,5) trisphosphate | 0.65 |
| Ins (1,4) bisphosphate | 0.9 |
| Ins (1,4,5) trisphosphate | 1.2 |
| Ins (1) monophosphate | 7.0 |
| Ins (2) monophosphate | 8.4 |

Ptd-Ins: Phosphatidyl-inositol (lipids)
Ins: Inositol (inositol phosphates)

What is claimed is:

1. A method for screening for a compound which modulates a signal response caused by a Pleckstin Homology (PH) domain of a signaling molecule comprising the steps of:

(a) incubating the compound with the PH domain of a signalling molecule which is capable of fluorescing;

(b) determining the phospholipid-induced modulation in the fluorescence of the PH domain, an alteration of the fluorescence in the presence of the compound being indicative of a functional interaction between the compound and the PH domain.

2. A method according to claim 1 wherein the fluorescence is associated with a Trp residue located in the N-terminus of the PH domain.

3. A method according to claim 1 wherein the signalling molecule is a protein kinase.

4. A method according to claim 3 wherein the signalling molecule is RAC protein kinase and the fluorescent residue is $Trp^{22}$.

5. A method according to claim 1 comprising incubating the candidate modulator compound with purified PH domain.

6. A method according to claim 5 wherein the PH domain is produced by expressing a recombinant expression vector encoding the PH domain as a GST fusion in a bacterial host cell, subsequently cleaving the GST fusion with thrombin and purifying the PH domain.

7. A method according to claim 4 wherein the PH domain is excited at 290 nm and fluorescence is detected at 345 nm.

* * * * *

UNITED STATES PATENT AND TRADEMARK OFFICE
CERTIFICATE OF CORRECTION

PATENT NO. : 6,054,285
DATED : April 25, 2000
INVENTOR(S) : Hemmings, et. al.

It is certified that error appears in the above-identified patent and that said Letters Patent is hereby corrected as shown below:

Claim 1, in column 23, second line of said claim should read:

-- lates a signal response caused by a Pleckstrin Homology --.

Signed and Sealed this

Twenty-seventh Day of February, 2001

Attest:

NICHOLAS P. GODICI

Attesting Officer

Acting Director of the United States Patent and Trademark Office

SEQUENCE LISTING

<160> NUMBER OF SEQ ID NOS: 23

<210> SEQ ID NO 1
<211> LENGTH: 2610
<212> TYPE: DNA
<213> ORGANISM: Homo sapiens
<220> FEATURE:
<221> NAME/KEY: CDS
<222> LOCATION: (199)..(1641)

<400> SEQUENCE: 1

```
atcctgggac aggcacagg gccatctgtc accaggggct tagggaaggc cgagccagcc       60
tgggtcaaag aagtcaaagg ggctgcctgg aggaggcagc ctgtcagctg gtgcatcaga      120
ggctgtggcc aggccagctg ggctcgggga gcgccagcct gagaggagcg cgtgagcgtc      180
gcgggagcct cgggcacc atg agc gac gtg gct att gtg aag gag ggt tgg        231
                     Met Ser Asp Val Ala Ile Val Lys Glu Gly Trp
                      1               5                  10 ctg cac aaa cga ggg gag tac atc aag acc tgg cgg cca cgc tac ttc        279
Leu His Lys Arg Gly Glu Tyr Ile Lys Thr Trp Arg Pro Arg Tyr Phe
            15                  20                  25 ctc ctc aag aat gat ggc acc ttc att ggc tac aag gag cgg ccg cag        327
Leu Leu Lys Asn Asp Gly Thr Phe Ile Gly Tyr Lys Glu Arg Pro Gln
        30                  35                  40 gat gtg gac caa cgt gag gct ccc ctc aac aac ttc tct gtg gcg cag        375
Asp Val Asp Gln Arg Glu Ala Pro Leu Asn Asn Phe Ser Val Ala Gln
    45                  50                  55 tgc cag ctg atg aag acg gag cgg ccc cgg ccc aac acc ttc atc atc        423
Cys Gln Leu Met Lys Thr Glu Arg Pro Arg Pro Asn Thr Phe Ile Ile
60                  65                  70                  75 cgc tgc ctg cag tgg acc act gtc atc gaa cgc acc ttc cat gtg gag        471
Arg Cys Leu Gln Trp Thr Thr Val Ile Glu Arg Thr Phe His Val Glu
                80                  85                  90 act cct gag gag cgg gag gag tgg aca acc gcc atc cag act gtg gct        519
Thr Pro Glu Glu Arg Glu Glu Trp Thr Thr Ala Ile Gln Thr Val Ala
            95                  100                 105
```

-continued

```
gac ggc ctc aag aag cag gag gag gag atg gac ttc cgg tcg ggc      567
Asp Gly Leu Lys Lys Gln Glu Glu Glu Met Asp Phe Arg Ser Gly
        110             115                 120 tca ccc agt gac aac tca ggg gct gaa gag atg gag gtg tcc ctg gcc  615
Ser Pro Ser Asp Asn Ser Gly Ala Glu Glu Met Glu Val Ser Leu Ala
    125                 130                 135 aag ccc aag cac cgc gtg acc atg aac gag ttt gag tac ctg aag ctg  663
Lys Pro Lys His Arg Val Thr Met Asn Glu Phe Glu Tyr Leu Lys Leu
140             145                 150                 155 ctg ggc aag ggc act ttc ggc aag gtg atc ctg gtg aag gag aag gcc  711
Leu Gly Lys Gly Thr Phe Gly Lys Val Ile Leu Val Lys Glu Lys Ala
                160                 165                 170 aca ggc cgc tac tac gcc atg aag atc ctc aag aag gaa gtc atc gtg  759
Thr Gly Arg Tyr Tyr Ala Met Lys Ile Leu Lys Lys Glu Val Ile Val
                175                 180                 185 gcc aag gac gag gtg gcc cac aca ctc acc gag aac cgc gtc ctg cag  807
Ala Lys Asp Glu Val Ala His Thr Leu Thr Glu Asn Arg Val Leu Gln
            190                 195                 200 aac tcc agg cac ccc ttc ctc aca gcc ctg aag tac tct ttc cag acc  855
Asn Ser Arg His Pro Phe Leu Thr Ala Leu Lys Tyr Ser Phe Gln Thr
        205                 210                 215 cac gac cgc ctc tgc ttt gtc atg gag tac gcc aac ggg ggc gag ctg  903
His Asp Arg Leu Cys Phe Val Met Glu Tyr Ala Asn Gly Gly Glu Leu
220                 225                 230                 235 ttc ttc cac ctg tcc cgg gaa cgt gtg ttc tcc gag gac cgg gcc cgc  951
Phe Phe His Leu Ser Arg Glu Arg Val Phe Ser Glu Asp Arg Ala Arg
                240                 245                 250 ttc tat ggc gct gag att gtg tca gcc ctg gac tac ctg cac tcg gag  999
Phe Tyr Gly Ala Glu Ile Val Ser Ala Leu Asp Tyr Leu His Ser Glu
                255                 260                 265 aag aac gtg gtg tac cgg gac ctc aag ctg gag aac ctc atg ctg gac  1047
Lys Asn Val Val Tyr Arg Asp Leu Lys Leu Glu Asn Leu Met Leu Asp
            270                 275                 280 aag gac ggg cac att aag atc aca gac ttc ggg ctg tgc aag gag ggg  1095
Lys Asp Gly His Ile Lys Ile Thr Asp Phe Gly Leu Cys Lys Glu Gly
        285                 290                 295 atc aag gac ggt gcc acc atg aag acc ttt tgc ggc aca cct gag tac  1143
Ile Lys Asp Gly Ala Thr Met Lys Thr Phe Cys Gly Thr Pro Glu Tyr
300                 305                 310                 315 ctg gcc ccc gag gtg ctg gag gac aat gac tac ggc cgt gca gtg gac  1191
Leu Ala Pro Glu Val Leu Glu Asp Asn Asp Tyr Gly Arg Ala Val Asp
                320                 325                 330 tgg tgg ggg ctg ggc gtg gtc atg tac gag atg atg tgc ggt cgc ctg  1239
Trp Trp Gly Leu Gly Val Val Met Tyr Glu Met Met Cys Gly Arg Leu
                335                 340                 345 ccc ttc tac aac cag gac cat gag aag ctt ttt gag ctc atc ctc atg  1287
Pro Phe Tyr Asn Gln Asp His Glu Lys Leu Phe Glu Leu Ile Leu Met
        350                 355                 360 gag gag atc cgc ttc ccg cgc acg ctt ggt ccc gag gcc aag tcc ttg  1335
Glu Glu Ile Arg Phe Pro Arg Thr Leu Gly Pro Glu Ala Lys Ser Leu
365                 370                 375 ctt tca ggg ctg ctc aag aag gac ccc aag cag agg ctt ggc ggg ggc  1383
Leu Ser Gly Leu Leu Lys Lys Asp Pro Lys Gln Arg Leu Gly Gly Gly
380                 385                 390                 395 tcc gag gac gcc aag gag atc atg cag cat cgc ttc ttt gcc ggt atc  1431
Ser Glu Asp Ala Lys Glu Ile Met Gln His Arg Phe Phe Ala Gly Ile
                400                 405                 410 gtg tgg cag cac gtg tac gag aag aag ctc agc cca ccc ttc aag ccc  1479
Val Trp Gln His Val Tyr Glu Lys Lys Leu Ser Pro Pro Phe Lys Pro
```

-continued

```
                 415                 420                 425
cag gtc acg tcg gag act gac acc agg tat ttt gat gag gag ttc acg    1527
Gln Val Thr Ser Glu Thr Asp Thr Arg Tyr Phe Asp Glu Glu Phe Thr
            430                 435                 440 gcc cag atg atc acc atc aca cca cct gac caa gat gac agc atg gag    1575
Ala Gln Met Ile Thr Ile Thr Pro Pro Asp Gln Asp Asp Ser Met Glu
    445                 450                 455 tgt gtg gac agc gag cgc agg ccc cac ttc ccc cag ttc tcc tac tcg    1623
Cys Val Asp Ser Glu Arg Arg Pro His Phe Pro Gln Phe Ser Tyr Ser
460                 465                 470                 475 gcc agc agc acg gcc tga ggcggcggtg gactgcgctg gacgatagct           1671
Ala Ser Ser Thr Ala
            480 tggagggatg gagaggcggc ctcgtgccat gatctgtatt taatggtttt tatttctcgg  1731
gtgcatttga gagaagccac gctgtcctct cgagcccaga tggaaagacg ttttgtgct   1791
gtgggcagca ccctccccccg cagcggggta gggaagaaaa ctatcctgcg ggttttaatt 1851
tatttcatcc agtttgttct ccgggtgtgg cctcagccct cagaacaatc cgattcacgt  1911
agggaaatgt taaggacttc tacagctatg cgcaatgtgg cattgggggg ccgggcaggt  1971
cctgcccatg tgtcccctca ctctgtcagc cagccgccct gggctgtctg tcaccagcta  2031
tctgtcatct ctctggggcc ctgggcctca gttcaacctg gtggcaccag atgcaacctc  2091
actatggtat gctggccagc accctctcct ggggtggca ggcacacagc agcccccag    2151
cactaaggcc gtgtctctga ggacgtcatc ggaggctggg cccctgggat gggaccaggg  2211
atggggatg ggccagggtt tacccagtgg gacagaggag caaggtttaa atttgttatt   2271
gtgtattatg ttgttcaaat gcattttggg ggttttttaat ctttgtgaca ggaaagccc  2331
cccccttccc cttctgtgtc acagttcttg gtgactgtcc caccggagcc tcccctcag   2391
atgatctctc cacggtagca cttgaccttt tcgacgctta accttccgc tgtcgcccca   2451
ggccctccct gactccctgt gggggtggcc atccctgggc cctccacgc ctcctggcca   2511
gacgctgccg ctgccgctgc accacggcgt tttttacaa cattcaactt tagtattttt   2571
actattataa tataatatgg aaccttccct ccaaattct                         2610
```

<210> SEQ ID NO 2
<211> LENGTH: 480
<212> TYPE: PRT
<213> ORGANISM: Homo sapiens

<400> SEQUENCE: 2

```
Met Ser Asp Val Ala Ile Val Lys Glu Gly Trp Leu His Lys Arg Gly
 1               5                  10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110
```

```
Gln Glu Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 3
``` cttgatgag                                                          9

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 4
aattctcatc aagccc                                                 16

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 5
gatccgctgg agc                                                    13

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 6
tagctccagc g                                                      11

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 7
gtggctgacg gcctctgag                                              19

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 8
aattctcaga ggccgtcagc cacagt                                      26

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 9 cttgatgag                                                              9

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 10
aattctcatc aagccc                                                      16

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 11
ggcaccggat ccgacgtggc tattgtgaag gagg                                  34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 12
ctcctgaatt cagaggccgt cagccacagt ctgg                                  34

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 13
gatccgctgg agc                                                         13

<210> SEQ ID NO 14
<211> LENGTH: 11
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 14
tagctccagc g                                                           11

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 15
aattctcact tcttgaggcc gtcagccaca gt                                    32

```
<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 16
ctgcaaaaga cgg                                                      13

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 17
cgctccgtct tttgcag                                                  17

<210> SEQ ID NO 18
<211> LENGTH: 37
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 18
gtggctgacg gcctcaagaa gcagaagaag aagtgag                            37

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide Linker

<400> SEQUENCE: 19
aattctcact tcttcttctg cttcttgagg ccgtcagcca cagt                    44

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:
      C-Terminal of pRSET PH110 Vector

<400> SEQUENCE: 20

Trp Thr Thr Ala Ile Gln Thr Val Ala Asp Gly Leu
  1               5                  10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence:
      C-Terminal of pRSET PH112 Vector

<400> SEQUENCE: 21

Trp Thr Thr Ala Ile Gln Thr Val Ala Asp Gly Leu Lys Lys
```

-continued

```
<210> SEQ ID NO 22
<211> LENGTH: 32
<212> TYPE: PRT
<213> ORGANISM: Artificial Sequence
<220> FEATURE:
<223> OTHER INFORMATION: Description of Artificial Sequence:
      C-Terminal of pRSET PH131 Vector

<400> SEQUENCE: 22

Trp Thr Thr Ala Ile Gln Thr Val Ala Asp Gly Leu Lys Lys Gln Glu
 1               5                  10                  15

Glu Glu Glu Met Asp Phe Arg Ser Gly Ser Pro Asp Asn Ser Gly Ala
            20                  25                  30

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: C-Terminal
      pRSET PH116 KKK  Vector

<400> SEQUENCE: 23

Trp Thr Thr Ala Ile Gln Thr Val Ala Asp Gly Leu Lys Lys Gln Lys
 1               5                  10                  15

Lys Lys
25
```